United States Patent [19]
Goertzen et al.

[11] Patent Number: 5,498,829
[45] Date of Patent: Mar. 12, 1996

[54] G1323 HARD WHITE WINTER WHEAT

[75] Inventors: Kenneth Goertzen; Betty Goertzen, both of Haven, Kans.

[73] Assignee: Cargill, Incorporated, Wayzata, Minn.

[21] Appl. No.: 269,003

[22] Filed: Jun. 30, 1994

[51] Int. Cl.[6] .............................. A01H 5/00; A01H 4/00; A01H 1/00; C12N 5/04
[52] U.S. Cl. ................. 800/200; 800/235; 800/DIG. 58; 435/240.4; 435/240.49; 435/240.5; 47/58; 47/DIG. 1
[58] Field of Search ..................................... 800/200, 205, 800/235; 47/58.03, 58, DIG. 1; 435/240.4, 145.49

[56] References Cited

PUBLICATIONS

Corpuz et al., "Relationship Between Kernel Color and Protein Content of Hard Red X Hard White Winter Wheat Progeny", Euphytica, 32:617–624 (1983).
Martin et al. (1993) *Registration of KS84HW195 Hard White Winter Wheat germplasm.* Crop Science, vol. 35, p. 1115.
Corpuz et al. (1984) *Relationship between Kernel Color and Protein Content of Hard red X hard White Winter Wheat Triticum–aestivum Progeny.* In Euphytica (1983) vol. 32(2) pp. 617–624. Biosis Abstract BA88:54609 cited.

*Primary Examiner*—Gary Benzion
*Attorney, Agent, or Firm*—Cargill, Incorporated

[57] ABSTRACT

A novel white winter wheat variety, designated G1323 that: is similar to or exceeds the best red wheats in high protein and gluten strength values; exhibits a milder flavor than typical red winter wheats; is resistant to sprouting in the head; is low intensity light tolerant, is hardy, resistant to insect infestations and other diseases, and may servive drought and winter chill conditions; may readily be cultivated in regions of the U.S. typically reserved for red wheat production; and yields commercially valuable brans in addition to flour extracts. This invention relates to the seeds of the G1323 variety, the wheat crops planted therefrom, and the hybrid wheat seeds and plants produced by crossing the G1323 variety with itself or another wheat variety.

6 Claims, 7 Drawing Sheets

G1323 HARD WHITE WINTER WHEAT

BACKGROUND OF THE INVENTION

The present invention relates generally to wheat production, and more specifically to a particular variety of hard white winter wheat designated G1323.

Wheat is an important crop as a food staple and nutritional agent, and has been cultivated since the times of ancient Egypt and Syria. Along with rice and corn, it accounts for about 75% of worldwide cereal production. In 1978, the United States produced 46% of the wheat in the global market.

Most white flour is milled from a mixture of different wheats. The proportion of each kind will typically depend upon a variety of factors, particularly the amount and proportion of protein contained therein. During the milling process, the endosperm portion of the wheat kernels is separated from the bran layers through a series of breaking and screening steps. While the resulting bran is commonly relegated to breakfast cereals or animal feeds, the endosperm fraction is ground to separate flour from the coarser endosperm particles. Finally, the flour is treated with bleaching and aging agents, enriched with vitamins, and packaged for both domestic and commercial end-users. While white flour intended for baking needs in domestic settings typically contains about 10.5% protein, commercial bakers generally desire a flour having a protein level around 11.5%, so that in the dough stage, it will withstand mechanical agitation imposed by commercial mixers.

Gluten is a complex of two primary endosperm proteins: gliadin and glutenin. Once the flour is moistened with water to make dough, these endosperm proteins will cooperate to form a complex throughout the mass. The elasticity of this protein complex permits the encapsulation of the carbon dioxide gas bubbles produced by the yeast or other levening agents added to the dough mixture.

Flour best suited for bread making contains proteins that form a gluten complex that will retain the shape of the bread not only during baking, but also after the bread cools. Moreover, bread bakers will generally desire a flour having a relatively high protein level to cause the bread to rise properly. On the other hand, bakers of cookies, cakes, and pastries will generally want a flour having a lower protein level and corresponding gluten strength, so that their products will not rise as much.

In order to fulfill these demands, flour millers are faced with a variety of wheats that are grown in different parts of the United States, depending upon soil and climate characteristics, and which provide different protein levels and properties. For example, soft red winter wheats are typically grown in Ohio, Indiana, and areas of the Southeastern U.S. Meanwhile, soft white wheats are generally grown in the Pacific Northwest and Michigan. Various analytical methods are available for measuring the "softness" or "hardness" of wheat kernels, and classifying the wheat varieties accordingly. Soft wheats typically have lower protein levels and protein characteristics that suit them more for cake and pastry baking than for bread baking.

"Hard" wheat varieties are characterized by the vitreous nature of their kernels. While there are instances of soft wheats that have protein levels higher than those of hard wheats (e.g., a soft red wheat variety developed by Goertzen Seed Research of Haven, Kans., and designated GRS2500 contains more protein than KARL, a hard wheat variety planted over a significant area of Western Kansas, and has actually been visually graded by federal inspectors as "hard"), the latter will generally have higher protein levels and gluten strength properties that are better suited for bread baking. Therefore, commercial bread bakers are generally biased in favor of flours made primarily from hard wheat varieties, and these varieties are demanded by flour millers accordingly. By controlling the amount of protein and quality of protein of the wheat that is blended into their flour, the bakers can regulate the size, shape, and consistency of their yeast-raised bread.

Hard red winter wheats are primarily grown in Kansas, Nebraska, Oklahoma, and Texas, and will have a red color in the intact wheat kernel and its outer layers. Hard red spring wheat is chiefly planted in Minnesota, North and South Dakota, and Montana. Both of these types of wheat varieties are widely used in flours for yeast-levened breads, and therefore comprise a substantial portion of all wheat used in flour.

However, in addition to their desirable protein and gluten properties, hard red wheats are characterized by a relatively strong wheat flavor that consumers may not want for whole wheat bread products. Moreover, the distinct red hue of whole wheat flour milled from hard red wheat varieties may be problematic for bread products like whole wheat croissants and Danish rolls that consumers typically associate with a white hue. Furthermore, bran separated from hard red wheat varieties is generally only suitable for animal feeds, and therefore is less valuable to the miller than brans derived from white wheat varieties that may be used in breakfast cereals and other bran products consumed by humans.

While white wheat varieties would fill these niches by producing a white whole wheat bread with a milder flavor, the fact remains that most white wheats are soft, with lower protein levels and lower gluten strength that are difficult to sell to millers for bread baking flour. Moreover, few hard white winter wheat varieties are adapted to hard red wheat areas of the U.S. (i.e., Kansas, Nebraska, Oklahoma, Minnesota, Texas, North and South Dakota, and Montana). Hard white winter wheat has only recently become a market class. The susceptibility of white wheat varieties to sprout in the head if wet conditions prevail during harvest time has also been a factor. If wheat sprouts in the head, it results in physical changes that lessen the bread making value of the wheat due to the development of atypical cell structure and slack dough, which causes the dough to run into the corners of a pan, instead of making slightly rounded corners of the loaf, and instead gives the part of the loaf that comes into contact with the pan a slick appearance.

Therefore, it would be useful to produce a variety of white wheat that is: (1) hard with higher protein levels and gluten strengths; (2) may be grown in the winter; (3) does not sprout in the head during damp conditions; and (4) has functional properties of protein that are good enough, and protein levels that are high enough to make good whole wheat bread products that lack the strong flavor of whole wheat products made from red wheats. Such a hard white wheat variety could be milled to higher flour extractions without creating objectionable color in the resulting flour, and the bran separated from the grain thereof could be readily marketed for breakfast cereals, instead of lower quality red wheat bran which must be marketed as lower priced livestock feed.

One way to produce such an altered wheat variety is through the application of plant breeding to existing white wheat varieties. By combining in a single variety various desirable traits like resistance to diseases and insects, tolerance to heat, drought, and cold spells, resistance to sprouting in the head, reducing the time to crop maturity, increasing plant yield, and improved agronomic quality, undesirable traits may be minimized, as well.

Wheat crops are bred by taking advantage of the plant's method of pollination. Ordinarily, the glumes enclosing the wheat blossom will prevent the pollen that originates from the anthers (male portion) of one plant from impregnating the ovule (female portion) of another nearby plant, such as when the wind blows. Thus, the pollen of a wheat plant will generally only impregnate the ovule of the same plant. This is called "self-pollination" and maintains the homozygous nature of the variety. The seed may also be replanted in a subsequent year to grow new wheat plants representative of that particular line.

A plant is cross-pollinated, however, if pollen on one plant is transferred to the flower of another plant to produce a uniform population of hybrid plants that may be heterozygous at many gene locations. The development of wheat hybrids requires the development of homozygous varieties, the crossing of these varieties, and the evaluation of the crosses. For example, two genotypes (i.e., varieties), each of which may have one or more desirable characteristics that is lacking in the other, or which compliment the other are first cross-pollinated to produce a hybrid progeny commonly designated $F_1$.

Next the superior $F_1$ plants are planted and self-pollinated to produce an $F_2$ group of plants. These plants are bulked and carried as a population. The $F_3$ generation may also be bulked, and carried as a population segregating into great diversity. Selections are often started in the $F_4$ generation and subsequent generations until a superior variety exhibiting the desired traits and none or few undesirable traits is obtained. This selection when uniform in appearance may then be self-pollinated through subsequent planting seasons to obtain an adequate amount of seed for commercial purposes.

SUMMARY OF THE INVENTION

Accordingly, it is an object of the present invention to provide a superior white winter wheat variety that is similar to the best red wheat in high protein and gluten strength of the resulting grain for bread baking purposes.

Another object of the present invention is to provide a white winter wheat variety for bread baking purposes that exhibits a milder flavor, whole wheat flour than the red winter wheat grains that are typically used by bakers for breads.

Yet another object of the present inventions to provide a white winter wheat variety for bread baking purposes that may be cultivated in regions of the United States that are typically reserved for red winter or spring wheat varieties, and that is specifically resistant to sprouting in the head if damp conditions prevail during the harvest season.

Still another object of the present invention is to provide a white winter wheat variety for bread baking purposes that is hardy, resistant to insect infestations and other diseases, and may survive drought and unexpectedly chilly conditions prior to harvest.

Yet another object of the present invention is to provide a white winter wheat variety that will yield a bran that is more commercially valuable than brans typically derived from hard red wheat varieties.

Other objects of the invention, in addition to those set forth above, will become apparent to those skilled in the art from the following disclosure.

Briefly, the invention is directed to providing a novel white winter wheat variety, designated G1323 that: is similar to or exceeds the best red wheats in high protein and gluten strength values; exhibits a milder flavor than typical red winter wheats; is resistant to sprouting in the head; is low intensity light tolerant, is hardy, resistant to insect infestations and other diseases, and may service drought and winter chill conditions; may readily be cultivated in regions of the U.S. typically reserved for red wheat production; and yields commercially valuable brans in addition to flour extracts. This invention relates to the seeds of the G1323 variety, the wheat crops planted therefrom, and the hybrid wheat seeds and plants produced by crossing the G1323 variety with itself or another wheat variety.

DETAILED DESCRIPTION OF THE PREFERRED EMBODIMENT

G1323 is a white winter wheat variety with superior characteristics, that have been found to be readily reproducible over successive planting seasons. It may be cultivated in predominately hard red winter wheat regions of the U.S. like Kansas, Colorado, South Dakota, Oklahoma, Nebraska, and Texas.

The G1323 variety was derived from a cross between a white seeded parent selected from J. R. Rupert's CIMMYT/ SCOUT population, and a red seeded winter wheat known as PLAINSMAN V. The Rupert seed production, in turn, results from a cross between a CIMMYT variety and SCOUT. The predominant characteristics of the Rupert seed were: (1) a hard white seeded, bearded, straw chaff, winter tender wheat of semi-dwarf stature; (2) phenotypical uniformity; (3) day-length insensitivity; (4) low test weight of the resulting grain; and (5) lower protein content. This final characteristic was problematic for bread baking capabilities. Low test weight of the grain was also a problem posed by the Rupert seed, because it tends to correspond to low flour recovery during milling, and therefore is undesirable to millers.

PLAINSMAN V resulted from a cross between two Goertzen Seed Research lines, one of which contained genetic information from Aegilops and Ovata. While the PLAINSMAN V wheat variety was a hard red winter wheat with the harsh flavor and lower value bran associated with that type of wheat, it also exhibited: (1) high yields; (2) genetically high protein levels; (3) outstanding blending qualities; (4) one of the first wheats known to have cephalasporium stripe resistance; (5) resistance to soil-borne/ spindle streak mosaic complex; (6) resistance to then prevalent races of leaf and stem rust; (7) mildew resistance; (8) insensitivity to day-length and low-light intensity; (9) early season maturity; (10)light red seed; and (11) winter hardiness. It should be stressed that the inventors of the present application were in a unique position to know the traits of the PLAINSMAN V red winter wheat, because they were the breeders thereof. Many of the listed attributes of PLAINSMAN V variety were not generally known in the trade.

The purpose of the cross was to combine the white seed coat of the Rupert selection with the outstanding protein and blending qualities of the PLAINSMAN V variety, while trying not to transfer the undesirable characteristic of each parent to the new variety. Once crossed, the resulting $F_1$ generation was bulked for further segregation. The subsequent $F_2$ and $F_3$ generations were handled as a bulk population in order to increase segregation into their diverse components. During the following $F_4$, $F_5$, and $F_6$ generations, single plants were selected. One of the white seeded selections made from the $F_6$ generation was found to be phenotypically homozygous, while exhibiting many of the desirable traits of the PLAINSMAN V variety. This particular selection was designated G1323.

Yield trials, quality evaluations, and observations were then made with the new G1323 variety. It met the criteria established by the inventors for a hard white winter wheat variety with outstanding crop and bread-making characteristics.

Figure 1:
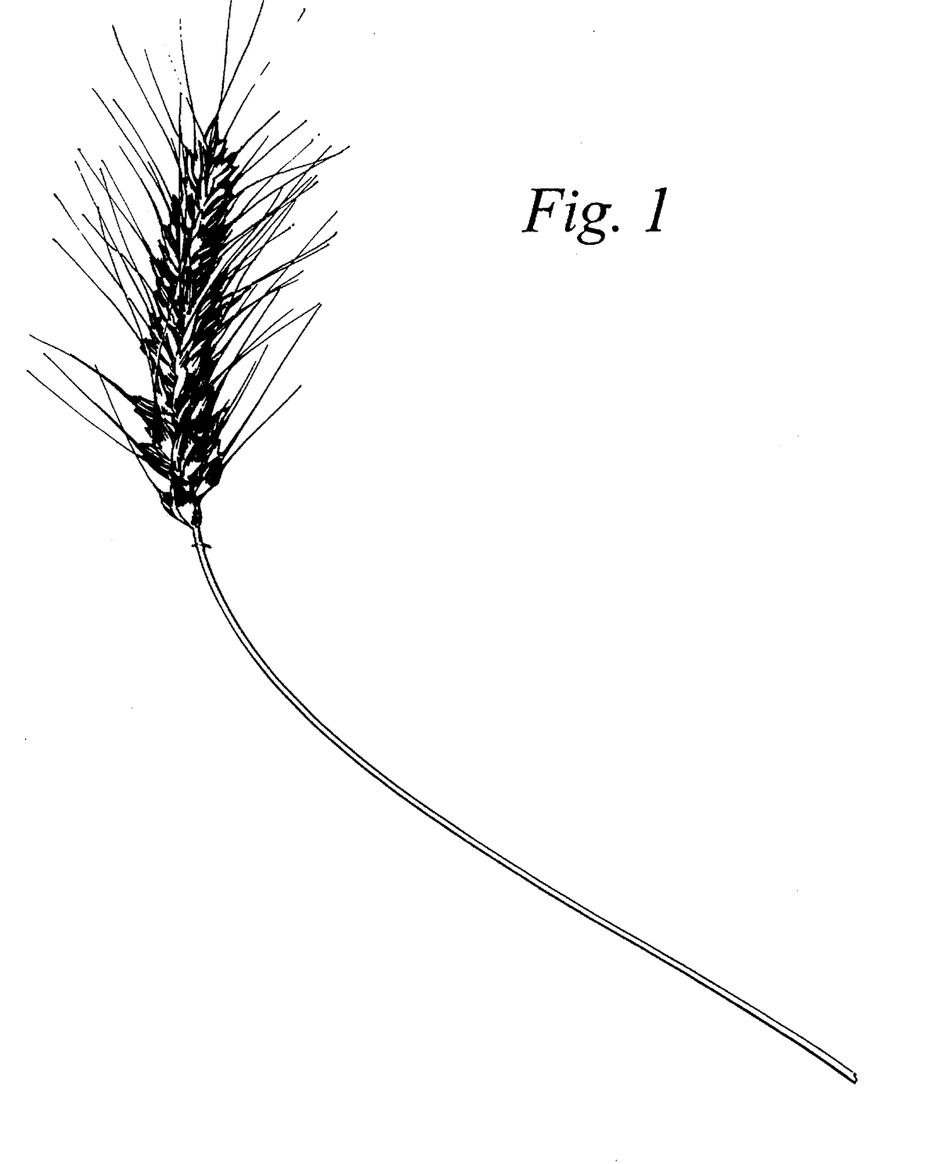

The G1323 variety shown in FIG. 1 is semi-dwarf in stature, early to very early in maturity with good winter hardiness. It is awned with brown glumes, and has an inclined head at maturity. It also has good straw strength. The G1323 variety also has been found to be a genetically high-protein wheat with excellent functional properties of the protein that makes it desirable for whole wheat products made without the addition of gluten.

For example, quality tests performed by Cargill, Incorporated have demonstrated that grain from the G1323 variety used in that test exhibited a wheat protein level at 12% moisture of 13.5%, a flour protein level at 14% moisture of 12.64%, a falling number value of 416, a percent flour extraction value of 74.5%, and a test weight of 59.5 lbs. The protein levels fall within the range of premium flours for bread baking purposes. Good bread baking wheat will often have a falling number between 400 and 500, so the 416 value for G1323 is desirable.

Similarly, good milling wheat will exhibit a flour extraction commercial average, based upon the weight of the milled wheat grain, of 72%, so the G1323 variety is slightly above average. Finally, the standard weight of a bushel of No. 1 hard red winter wheat is 60 lbs., so the 59.5 lb value for the G1323 variety compares very favorably with hard red winter wheat in this respect as well.

The United States Department of Agriculture's Grain Marketing Research Center has conducted blind tests on different wheat varieties, and the results for a number of the tested varieties are reproduced in Table 1 shown below.

TABLE 1

| U.S.D.A. Identification Number | Kind | Wt/ Bushel (lbs) | 1000 Kernel Weight (g) | Kernel Sizing Large % | Kernel Sizing Medium % | Kernel Sizing Small % | SKWCS- Average Kernel Moisture % | SKWCS- Average Kernel Weight (mg) | SKWCS- Average Kernel Diam (mm) | Hardness Score SKWCS | Hardness Score NIR | Actual Identity of Variety |
|---|---|---|---|---|---|---|---|---|---|---|---|---|
| LB93-0001 | HWW | 59.4 | 37.5 | 70.0 | 30.0 | 0.0 | 13.8 | 40.1 | 3.12 | 71 | 60 | G2044 |
| LB93-0005 | HRW | 60.0 | 32.6 | 63.0 | 57.0 | 0.0 | 12.6 | 34.1 | 2.91 | 81 | 84 | HAVEN |
| LB93-0007 | HRW | 59.1 | 30.9 | 36.0 | 64.0 | 0.0 | 12.8 | 31.9 | 2.78 | 67 | 64 | G2160 |
| LB93-0008 | HWW | 57.8 | 29.4 | 23.0 | 77.0 | 0.0 | 12.9 | 32.0 | 2.73 | 65 | 60 | G1323 |
| LB93-0010 | HRW | 60.3 | 35.0 | 69.0 | 31.0 | 0.0 | 13.2 | 37.0 | 2.99 | 76 | 85 | G1878 |
| LB93-0016 | HRW | 60.0 | 34.2 | 67.0 | 33.0 | 0.0 | 13.4 | 35.9 | 2.97 | 77 | 80 | G1891 |
| LB93-0017 | HWW | 57.7 | 29.5 | 36.0 | 65.0 | 1.0 | 13.2 | 36.2 | 2.89 | 78 | 75 | G1317 |
| LB93-0035 | SRW | 60.5 | 35.2 | 68.0 | 32.0 | 0.0 | 12.9 | 35.8 | 2.99 | 27 | 25 | GSR2500 |
| LB93-0045 | HRW | 58.2 | 34.5 | 55.0 | 45.0 | 0.0 | 13.0 | 34.4 | 2.99 | 78 | 82 | G2542 |
| LB93-0046 | HRW | 59.7 | 32.5 | 44.0 | 56.0 | 0.0 | 12.7 | 35.0 | 2.93 | 84 | 86 | ADVANTAGE |
| LB93-0047 | HRW | 58.2 | 32.0 | 57.0 | 43.0 | 0.0 | 13.1 | 34.2 | 3.03 | 57 | 47 | AGSECO 7853 |
| LB93-0048 | HRW | 58.0 | 32.4 | 25.0 | 74.0 | 1.0 | 13.1 | 32.0 | 2.85 | 67 | 66 | KARL |
| LB93-0049 | HRW | 57.3 | 31.6 | 56.0 | 43.0 | 1.0 | 13.4 | 31.9 | 2.86 | 66 | 64 | VICTORY |

LEGEND:
HRW = Hard Red Wheat
HWW = Hard White Wheat
SRW = Soft Red Wheat
"Large" = Ca. 40 g/1000 Kernels
"Medium" Ca. 30 g/1000 Kernels
"Small" Ca. Below 30 g/1000 Kernels Two different methods for measuring hardness of the wheat kernel were used by the USDA. The SKWCS method mechanically measures the hardness of a single kernel. The higher the score, the harder the wheat kernel. The NIR method is a near infra-red measurement of hardness. Once again, a higher number indicates a higher hardness level. The results indicate that the G1323 variety of the present invention scored SKWCS and NIR hardness scores of 65 and 60, respectively, that were far higher than the 27/25 score of GSR 2500, a soft red wheat, and very comparable with the scores posted by the hard red wheats, including KARL, which is widely planted in the grain belt.

Figure 2:
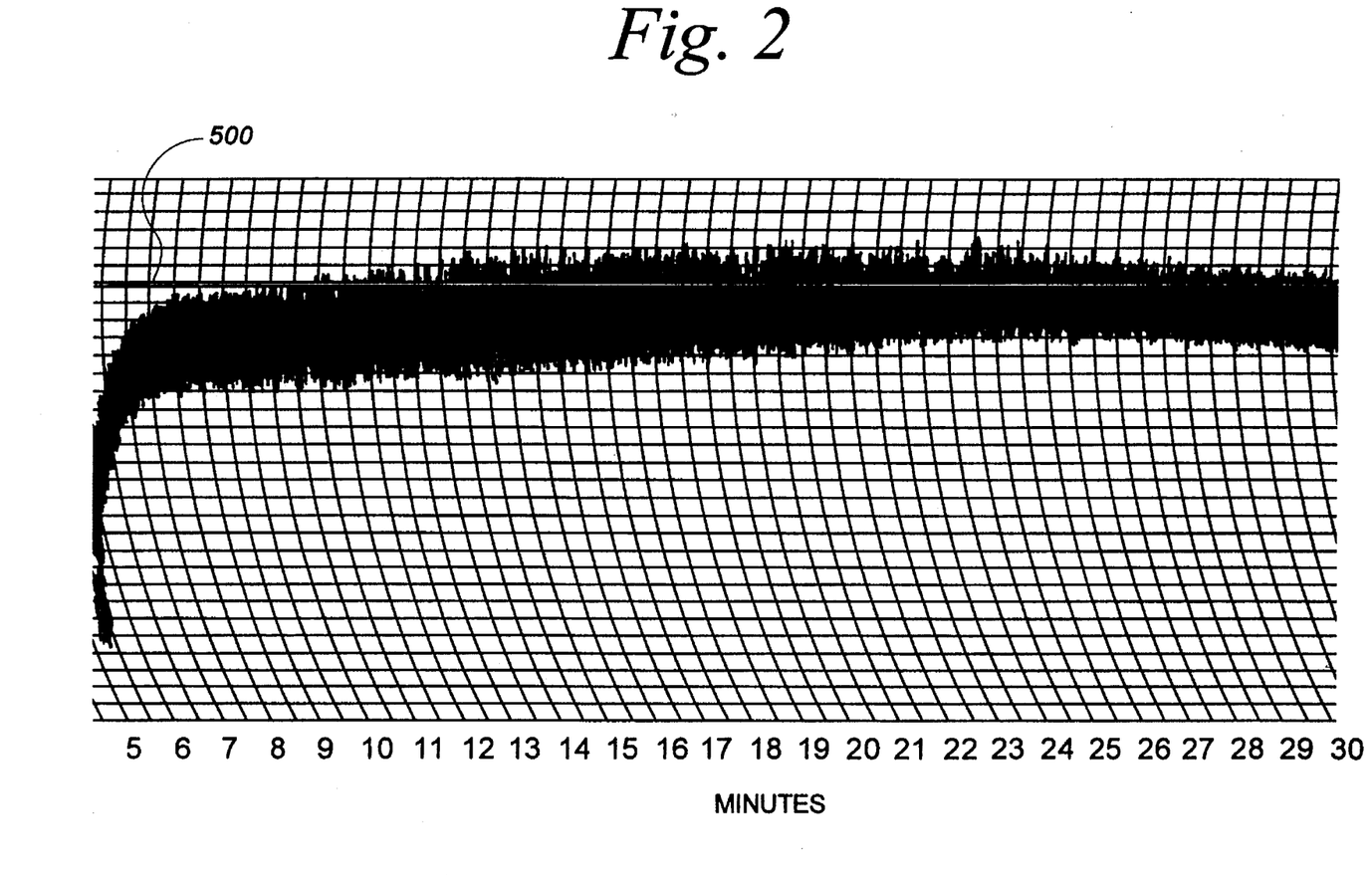

Similarly, dough made from flour milled from the G1323 variety performs very well. FIG. 2 shows a farinograph from Cargill's laboratory for this variety, which is essentially a measure of the ability of the flour to absorb and retain water over time. Bakers frequently use farinographs to measure the rheological properties of their flours, and therefore prodict the physical properties of doughs made from such flours. The longer the farinograph curve stays at or above the Barbender 500 unit line, commonly called the "consistency line", the better the strength and blending quality of the dough. In the present case, the G1323 variety flour approaches the consistency line and stays at or above it for a prolonged period of time. Indeed, this particular farinograph shows a time for arrival at the consistency line of 5.5 minutes, an elapsed time for the curve to peak of 19.5 minutes, an elapsed time for the curve to depart below the consistency line of 26.75 minutes, an elapsed time in which the dough is stable between the arrival and departure times of 21.25 minutes, and a M.T.I. score of 30. Because typical wheat will typically exhibit a peak time of 5–8 minutes, a departure time of 10–15 minutes, and a stability time of 10–15 minutes, these results show that the G1323 variety is outstanding for bread baking.

Furthermore, various tests run on bread actually baked from dough made from the G1323 variety using the sponge dough method demonstrate the superior bread-making capabilities of this variety. One measure is "bake volume", which is the volume of a loaf of bread baked from a 160 g of dough placed in a shogren standard puppan. A score of 800 cc. is deemed acceptable for good bread. Bread made from the G1323 variety scored 1000 cc.

Next a "bake score" comprising the aggregate scores of a variety of individual evaluative measurements like absorption, volume, dough handling, make up, mix tolerance, grain, texture, and crumb color is taken. A score in the upper 70's is outstanding. Bread made from the G1323 variety scored a 72.

Finally, "bake strength" is a subjective determination of the flour's gluten quality. A trained evaluator takes the dough out of the mixer after the remix stage, and determines its strength on a 0–100 scale. A score of 60 is considered to show a moderately strong gluten wheat. A score of 80 is correlative of a strong gluten wheat that will make whole wheat bread of good quality. A score of 100, on the other hand, indicates a super strong gluten wheat that can be used in blends to enhance bread-making. Table 2 shows the results of a blind test conducted by Cargill's laboratory on a number of wheat varieties.

While white wheats traditionally are more susceptible to sprouting in the head in the field than are hard red wheats, the G1323 variety showed good resistance to spouting in the head under excessive moisture conditions at harvest in 1989 and 1992—even the flood conditions that prevailed in the Midwestern region of the U.S. in Summer 1993. Moreover, the G1323 variety has demonstrated resistance to sudden drops in temperature, such as temperature drops during February 1989, and winter kill conditions. The variety likewise is moisture stress tolerant, having survived drought conditions.

The G1323 variety is also relatively tolerant of conditions characterized by low light intensity. Plants have been grown from G1323 seed in shelters covered by semi-translucent plastic with satisfactory results, and without the use of supplemental lighting sources.

Moreover, the G1323 variety is resistant to prevalent races of stem rust, soil-borne mosaic virus, and soil-borne/spindle streak virus complex. It shows moderate resistance to powdery mildew, as well as to common root rots. The G1323 variety is susceptible to barley yellow dwarf mosaic.

A more detailed description of the G1323 variety is provided in Table 3.

TABLE 2

| Variety | Kind | States Adapted | Water Absorbed by Dough (%) | Mix Time (min) | Volume | Grain & Texture | Bake Streghth[r] |
|---|---|---|---|---|---|---|---|
| G1323 | HWW | KS | 62.0 | 13 | 985 | 78 | 100 |
| TRAFALGAR | HRW | KS, SPAIN | 62.5 | 11 | 1,010 | 77 | 80 |
| G825[1] | HRW | KS | 62.0 | 12 | 975 | 72 | 80 |
| G825[1] | HRW | KS | 62.5 | 12 | 950 | 72 | 100 |
| G62 | HRW | KS, OK | 62.5 | 11 | 940 | 72 | 100 |
| G1753 | HRW | KS, OK | 62.5 | 12 | 1,065 | 72 | 100 |
| G1782 | HRW | KS, OK | 63.0 | 13 | 980 | 72 | 100 |
| G1781 | HRW | KS, OK | 63.5 | 12 | 1,050 | 72 | 100 |
| G1420[2] | SRW | KS, OK, MO | 62.0 | 12 | 1,000 | 72 | 100 |
| G1056 | SRW | KS | 63.0 | 10 | 990 | 72 | 80 |
| G3000 | HRW | KS | 63.0 | 12 | 1,015 | 72 | 80 |
| G1781 | HRW | KS | 63.5 | 12 | 1,030 | 72 | 100 |
| WL9104[3] | RW | KS | 62.0 | 11 | 980 | 67 | 100 |
| HAVEN | HRW | KS, OK, CO | 63.0 | 11 | 950 | 67 | 60 |
| G1783 | HRW | Hard Winter Wheat area | 63.0 | 11 | 1,025 | 67 | 60 |
| G1895 | HRW | Hard Winter Wheat area | 62.5 | 12 | 1,000 | 67 | 100 |
| G1816 | HRW | KS | 62.0 | 12 | 970 | 67 | 80 |
| G1785 | HRW | Hard Winter Wheat area | 63.0 | 13 | 990 | 67 | 100 |
| DISCOVERY | HRW | KS | 63.0 | 13 | 1,035 | 67 | 100 |
| G1990 | HRW | MT | 63.0 | 12 | 950 | 67 | 100 |
| G1009 | HRW | KS, OK | 63.0 | 10 | 970 | 67 | 80 |
| PLAINSMAN V | HRW | Hard Winter Wheat area | 63.0 | 13 | 970 | 67 | 100 |
| KARL | HRW | KS, OK, MO | 62.5 | 13 | 1,015 | 62 | 100 |
| VOYAGER | HRW | MT | 63.0 | 12 | 950 | 62 | 100 |

1. One of these was grown about ¼ mile from the others.
2. Has a higher 3-year average yield than any soft or hard wheat check grown by Goertgen Seed Research.
3. Hybrid.
4. Twenty-one other wheat varieties had bake scores of 62.

These results show that the G1323 variety's bake strength score was 100, which indicates super strong gluten wheat. Moreover, it is equal to several hard red wheat varieties like PLAINSMAN V, KARL, VOYAGER, and DISCOVERY, and actually exceeds those of other hard red wheat varieties like TRAFALGAR, G3000, HAVEN, G1783, G1816, and G1009. This is the crux of the new G1323 variety: it is a hard white winter wheat variety that has protein and gluten levels that meet or exceed those of the hard red wheats widely used for bread-baking purposes.

TABLE 3

G1323 VARIETY DESCRIPTION INFORMATION

A. General
  Type: White Winter Wheat
  Region Best Adopted: Kansas, South Dakota, Montana, Nebraska, Oklahoma, Texas
B. Plant Characteristics
  Growth Habit: winter Coleoptile Color: white
Coleoptile Expression: medium
Emergence: excellent emergence of seedling when planted 4 inches deep
Juvenile Growth Habit: semi-erect
Color at Boot: green
Flag Leaf at Booting: erect, twisted with no waxy bloom
First Leaf Below Flag Leaf: mid-wide (11 to 12 mm.) mid-long to long (21 to 32 cm length)
Auricles: white with no pubescence present
Time to Heading: early to very-early
Stem: mid-strong; no waxy bloom; hollow internodes; pubescence present on last internode of rachis
Plant Height: medium-short (92.5 cm average)

C. Spike
Mid-long (8–9 cm)
Mid-wide (10–12 mm)
Shape: tapering
Density: mid-dense
Position at Maturity: inclined
Color of awns at Maturity: tan D. Glumes
Color at Maturity: brown
Length: long (6–9 mm)
Width: narrow (3–3.5 mm)
Shoulder: narrow (1–1.5 mm)
Shape: oblique E. Beak
Width: narrow (to 1 mm)
Length: very long (6 to 9 mm)
Shape of Apex: acuminate F. Seed Characteristics
Color: amber (white seed appears to be amber when grain is high in protein).
Size: mid-long (6.5–7.5 mm)
mid-wide (2.5–3.5 mm)
Shape: ovate
Brush Size: small
Brush Length: medium (0.5–1.0 mm)
Brush not collared
Crease Width: narrow
Crease Depth: shallow
Cheek: rounded (not angular)
Germ: large
Texture: hard
HMW Glutenin Subunits: 2*, 5, 10, 17, 18

G. Anther and Pollen Shed
Anther is extruded from the glumes at blossoming, and pollen shed is sufficient if used as a female maintainer, or in hybrid production.

H. Diseases
Stem Rust: resistant
Soil-Borne Mosaic Virus: resistant
Soil-Borne/Spindle Streak Virus Complex: resistant
Powdery Mildew: moderate resistance
Common Root Rot: moderate resistance
Barley Yellow Dwarf Mosaic: susceptible I. Electrophoresis Results
2*, 5, 10, 17, 18 (all five of these high molecular weight glutenin subunits are associated with good bread quality)

The seed from the G1323 variety, the plant produced therefrom, a hybrid wheat plant produced from crossing the G1323 variety, hybrid seed, and various parts of the hybrid wheat plant are within the scope of this invention, and may be used for human and animal foods.

Only two other hard white winter wheats are presently grown in the hard red winter wheat growing region. They are ARLIN, a publicly available variety developed by plant breeders at Kansas State, and RIO BLANCO developed by AgriPro Biosciences. The outstanding differences between the G1323 variety and the ARLIN and RIO BLANCO varieties are as follows:

1. G1323 has genetically high protein and gluten levels equal to that of the hard red winter wheat variety designated KARL that was developed by plant breeders at Kansas State University based upon the PLAINSMAN V variety, and is planted widely in Kansas. By contract, gluten must be added to flour milled from both ARLIN and RIO BLANCO to bake acceptable whole wheat bread.

2. G1323 is resistant to sprouting in the head which is common to most white wheats. Both ARLIN and RIO BLANCO are susceptible to sprouting in the head.

3. G1323 has better mildew resistance than those hard white winter wheat varieties presently on the market, including ARLIN and RIO BLANCO.

4. G1323 has winter hardiness that is superior to ARLIN's, and leaf rust resistance that exceeds that of RIO BLANCO.

5. G1323 has a semi-erect juvenile growth habit, while ARLIN shows a more erect habit;

6. G1323's plant color at boot stage is green, while ARLIN's is blue green with a waxy bloom, and RIO BLANCO's is yellow green.

Based upon visual observations of G1323, ARLIN, and RIO BLANCO varieties planted side by side in drill strips in Haven, Kans., a more exact comparison of these three hard white winter wheat varieties is presented in Table 4.

TABLE 4

|  | G1323 | ARLIN | RIO BLANCO |
|---|---|---|---|
| Plant Color at Boot Stage | Green | Blue Green | Yellow Green |
| Flag Leaf at Boot Stage | Erect | Erect | Slight Drooping |
| average length | 17.25 cm | 14.75 cm | 18 cm |
| average width | 12 mm | 12 mm | 11 mm |
| Leaf Below Flag Leaf |  |  |  |
| length | 21.5 cm | 15.25 cm | 20.5 cm |
| width | 10 mm | 11.5 cm | 10.5 mm |
| Nodes Above Ground | 3.00 | 3.00 | 3.00 |
| Tillering | Good | Good | Good |
| Head Length to Awns | 9 cm | 8.5 cm | 9 cm |
| Head Length With Awns | 15.5 cm | 15 cm | 14.5 cm |
| Fertile Florets | 16.00 | 15.00 | 15.00 |
| Glume Color | Brown | White | White |
| Maturity | Early | Early | Midseason |

These three hard white winter wheat varieties have also been reported to have the following high-molecular weight glutenin subunits, based upon electrophoresus patterns:

RIO BLANCO heterozygous: 2*, 5, 10, (heterozygous for 7, 8, 13, 19)

ARLIN: 2*, 5, 10, 7, 9

G1323: 2*, 5, 10, 17, 18

Figure 3:
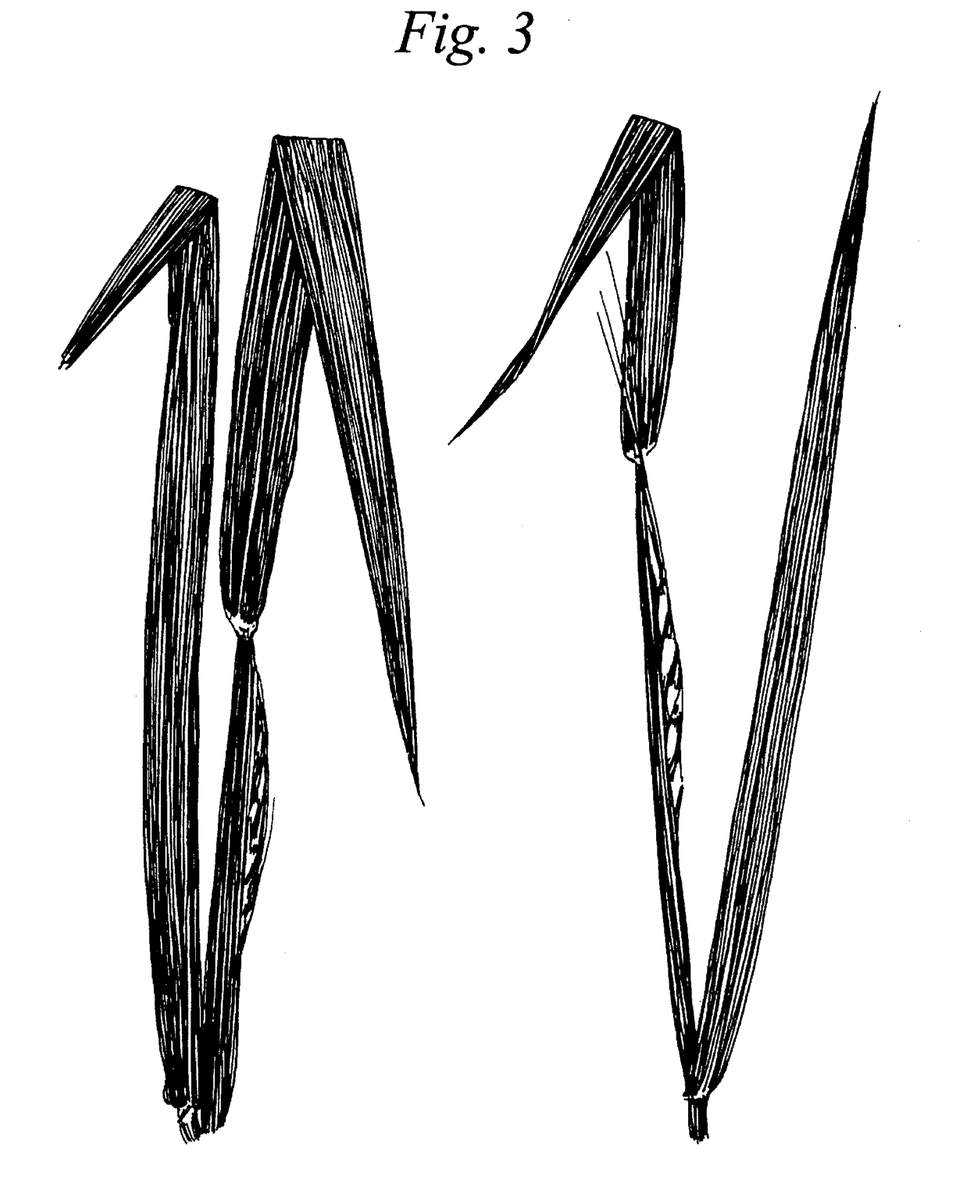
Figure 4:
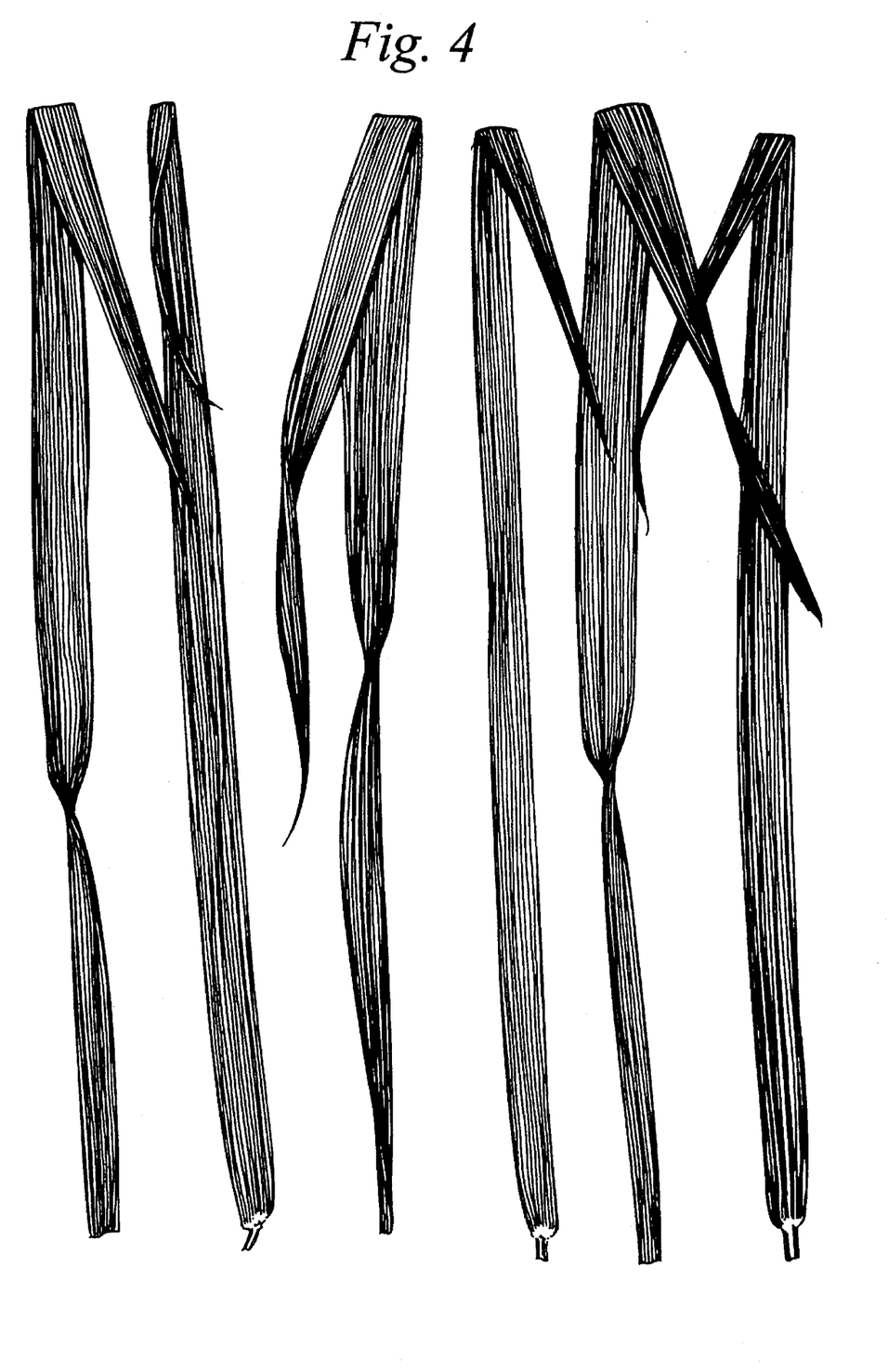
Figure 5:
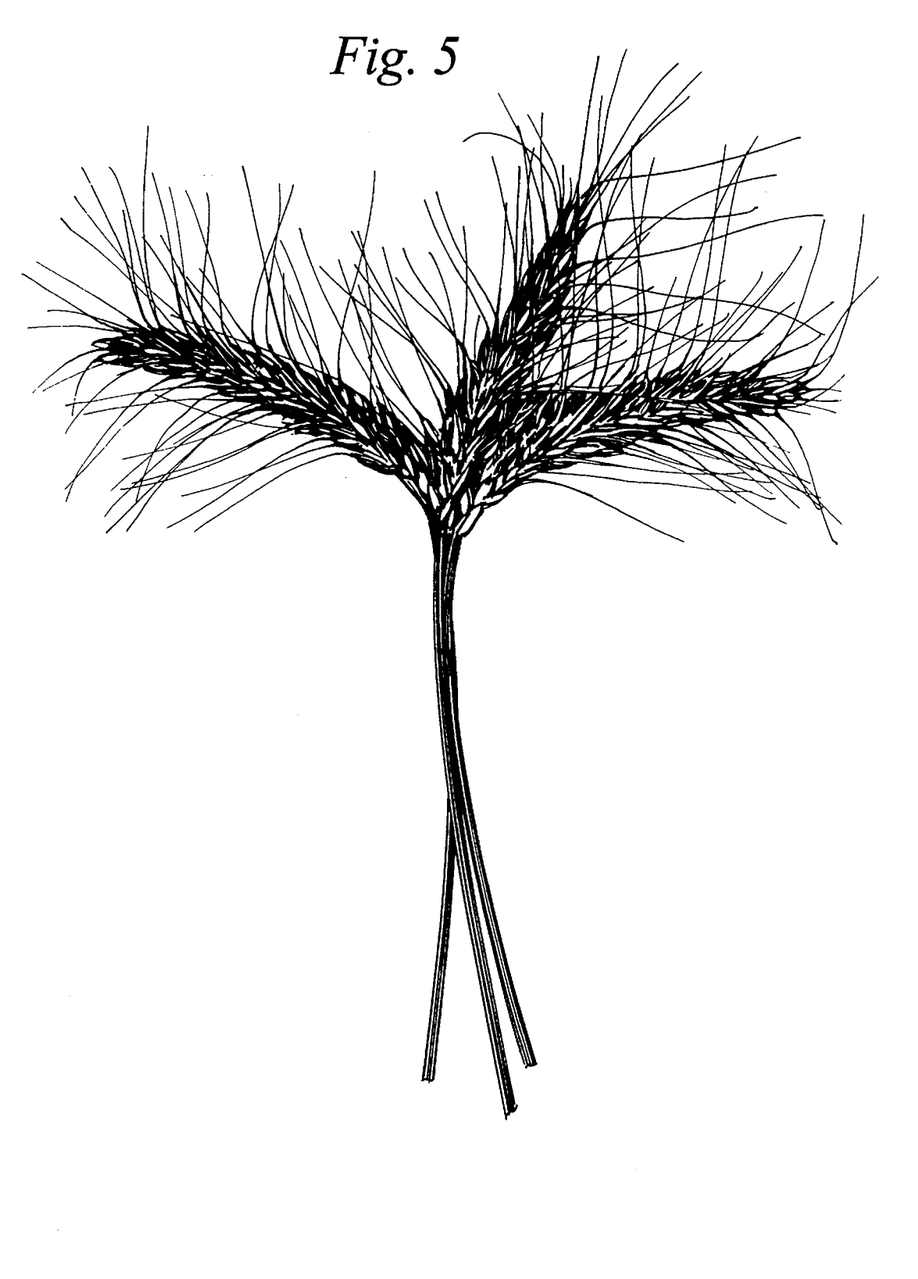
Figure 6:
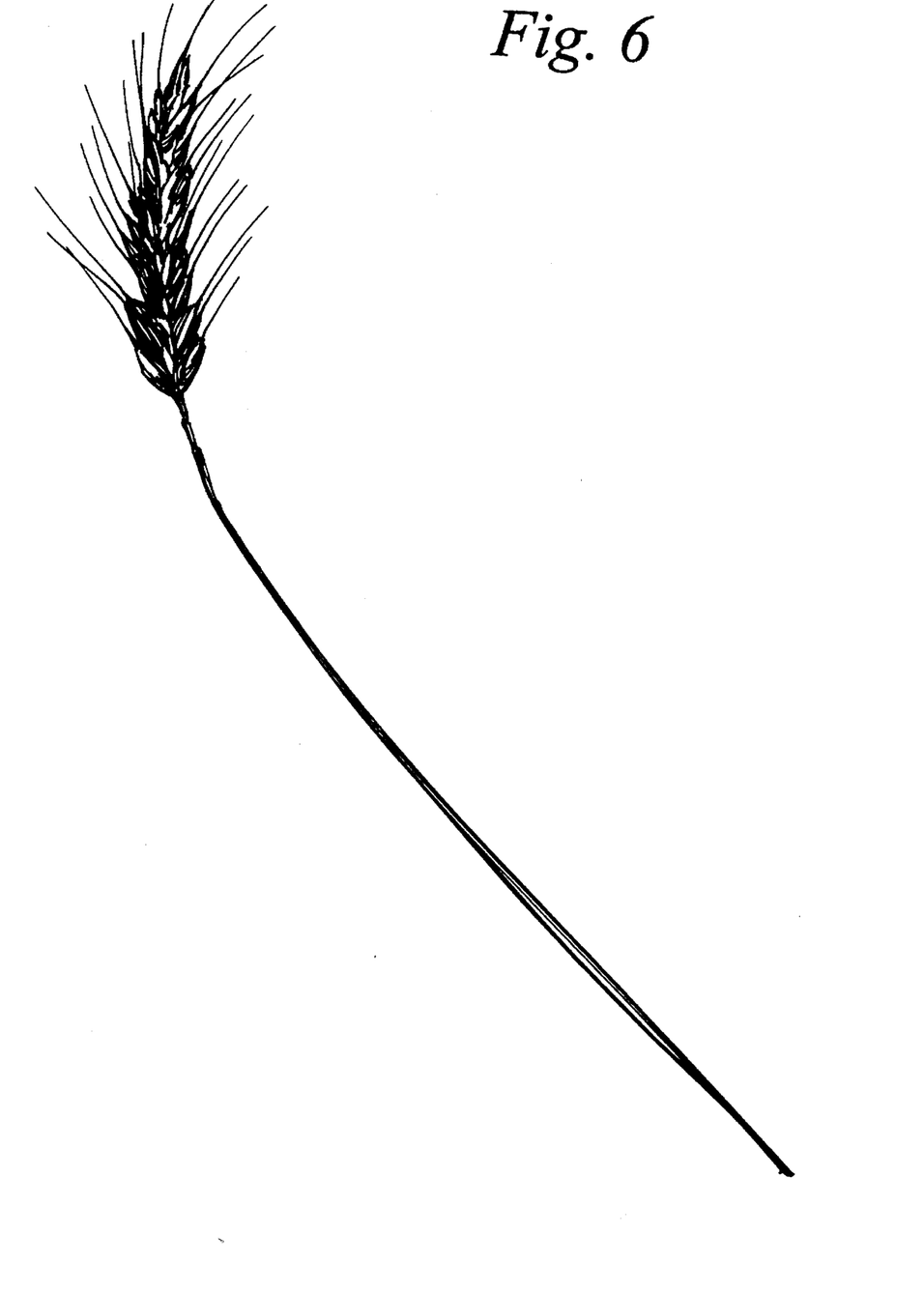
Figure 7:
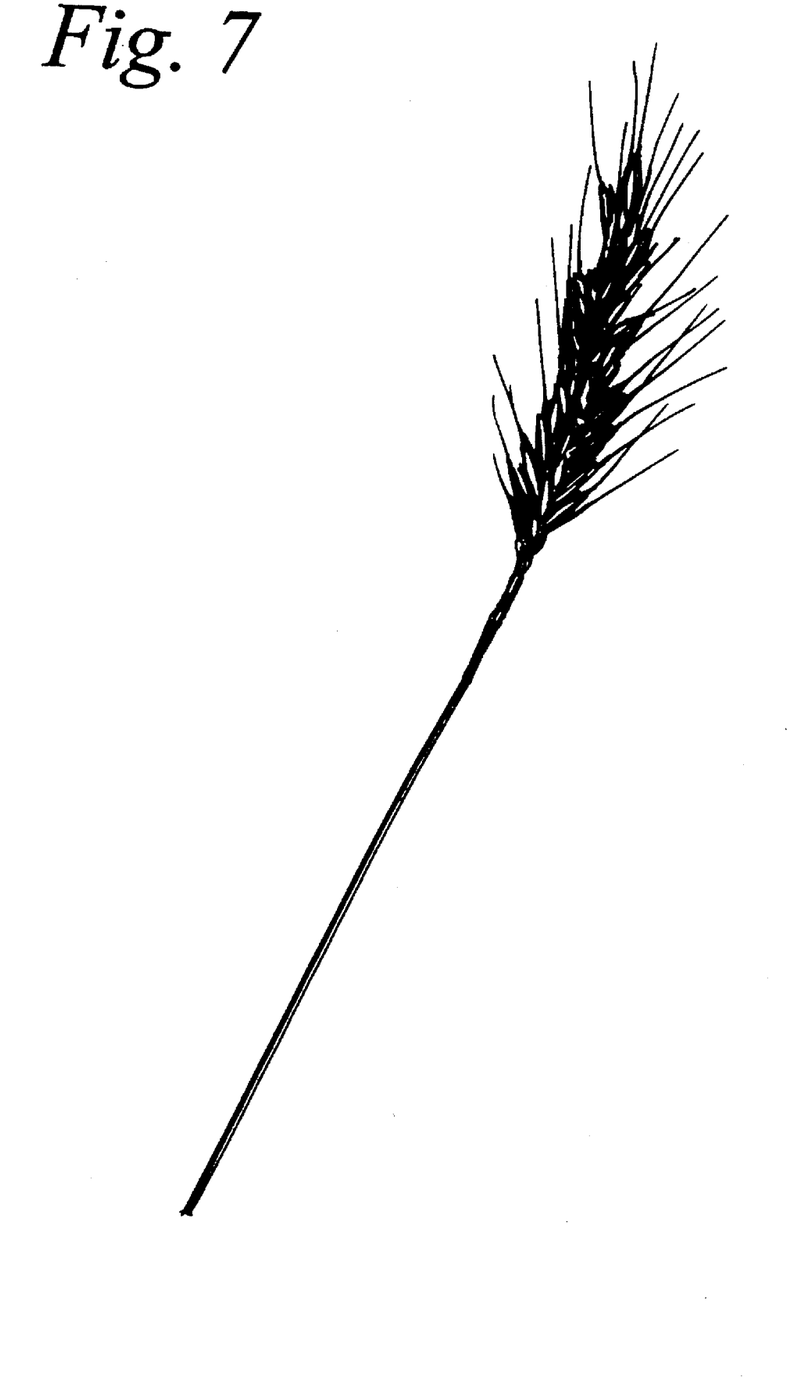

Actual plants of the G1323 variety are shown at boot stage, early maturity stage and full bloom stage in FIGS. 3, 4, and 5, respectively. Moreover, actual plants of the ARLIN and RIO BLANCO varieties are shown in FIGS. 6 and 7.

Applicants will make available to the public without restriction a deposit of at least 2500 seeds of the G1323 variety with the American Tissue Culture Collection (ATCC), Rockville, Md. 20852 U.S.A., ATCC Deposit No.

97217. The seeds to be deposited with the ATCC will be taken from the same deposit maintained by Cargill, Incorporated's Goertzen Seed Research subsidiary, 6 Stadium Drive, Haven, Kans. 67543 since prior to the filing of this application. The deposit will be maintained at the ATCC depository, which is a public depository, for a period of 30 years, or 5 years after the most recent request, or for the effective life of the patent, whichever is longer, and will be replaced if it becomes nonviable during that period.

While particular embodiments of the invention have been shown and described, it should be understood that the invention is not limited thereto, since many modifications may be made. The invention is therefore contemplated to cover by the present application any and all such modifications which fall within the time spirit and scope of the basic underlying principles disclosed and claimed herein.

What is claimed is:

1. A hard white winter wheat seed designated G1323, having ATCC Accession No. 97217.

2. A wheat plant produced by the seed of claim 1.

3. A tissue culture of cells from the plant of claim 2.

4. Tissue culture as recited in claim 3, comprising regenerable cells of a plant part selected from meristematic tissue, anthers, leaves, embryos, pollen and protoplasts therefrom.

5. A wheat plant regenerated from the regenerable cells of a tissue culture according to claim 4, said regenerated plant having the characteristics of drought tolerance, winter hardiness, day-length insensitivity, and low-light tolerance as found in wheat plant G1323 having ATCC Accession No. 97217.

6. A hard white winter wheat plant having all of the physiological and morphological characteristics of the plant of claim 2.

* * * * *